(12) United States Patent
Kageyama et al.

(10) Patent No.: US 10,982,179 B2
(45) Date of Patent: Apr. 20, 2021

(54) DIETARY FIBER

(71) Applicant: SUNTORY HOLDINGS LIMITED, Osaka (JP)

(72) Inventors: Norihiko Kageyama, Kawasaki (JP); Keiko Shimamoto, Kyoto (JP); Takehiro Watanabe, Kyoto (JP); Tohru Yamagaki, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 110 days.

(21) Appl. No.: 15/539,287

(22) PCT Filed: Jan. 9, 2015

(86) PCT No.: PCT/JP2015/050525
§ 371 (c)(1),
(2) Date: Jun. 23, 2017

(87) PCT Pub. No.: WO2016/103737
PCT Pub. Date: Jun. 30, 2016

(65) Prior Publication Data
US 2017/0349867 A1   Dec. 7, 2017

(30) Foreign Application Priority Data
Dec. 26, 2014 (JP) .............................. JP2014-266551

(51) Int. Cl.
*C12G 3/06* (2006.01)
*C12C 12/00* (2006.01)
(Continued)

(52) U.S. Cl.
CPC ................ *C12G 3/06* (2013.01); *A23L 2/382* (2013.01); *A23L 2/52* (2013.01); *A23L 2/54* (2013.01);
(Continued)

(58) Field of Classification Search
CPC ....... A23L 33/21; A23L 29/212; C08B 30/18; C08B 37/0009
See application file for complete search history.

(56) References Cited

U.S. PATENT DOCUMENTS 3,876,794 A   4/1975  Rennhard
4,622,233 A   11/1986 Torres
(Continued)

FOREIGN PATENT DOCUMENTS

EP   1 582 102 A1   10/2005
JP   H04-43624 B2   7/1992
(Continued)

OTHER PUBLICATIONS

International Preliminary Report on Patentability dated Jun. 27, 2017 for PCT/JP2015/050525.
(Continued)

*Primary Examiner* — Vera Stulii
(74) *Attorney, Agent, or Firm* — Faegre Drinker Biddle & Reath LLP (57) ABSTRACT

Provided is a dietary fiber characterized in that bitterness and unpleasant aftertaste are restrained. The dietary fiber has terminal sugars and is characterized in that the ratio of aldoses relative to the total of the terminal sugars is 10% or less. Such a dietary fiber may be, for example, indigestible dextrin, polydextrose or the like. The dietary fiber may be used as a food additive (for example, a beverage additive).

27 Claims, 1 Drawing Sheet (51) Int. Cl.
    A23L 2/38      (2021.01)
    A23L 2/54      (2006.01)
    C12C 5/02      (2006.01)
    C12G 3/00      (2019.01)
    A23L 2/52      (2006.01)
    C08B 30/18     (2006.01)
    A23L 33/21     (2016.01)
    A23L 2/56      (2006.01)

(52) U.S. Cl.
    CPC .............. *A23L 2/56* (2013.01); *A23L 33/21* (2016.08); *C08B 30/18* (2013.01); *C12C 5/02* (2013.01); *C12C 12/00* (2013.01); *C12G 3/00* (2013.01); *C12G 2200/21* (2013.01)

(56) References Cited

U.S. PATENT DOCUMENTS

| | | | |
|---|---|---|---|
| 5,601,863 | A | 2/1997 | Borden et al. |
| 5,620,873 | A | 4/1997 | Ohkuma et al. |
| 2005/0220845 | A1 | 10/2005 | Kishimoto et al. |
| 2007/0190113 | A1 | 8/2007 | Kishimoto et al. |
| 2009/0239823 | A1 | 9/2009 | Kishimoto et al. |

FOREIGN PATENT DOCUMENTS

| | | |
|---|---|---|
| JP | H06-500145 A | 1/1994 |
| JP | H06-32802 A | 2/1994 |
| JP | 2001-299227 A | 10/2001 |
| JP | 2004-065128 A | 3/2004 |
| JP | 2009-017867 A | 1/2009 |
| JP | 2009-028019 A | 2/2009 |
| JP | 2013-252075 A | 12/2013 |

OTHER PUBLICATIONS

"Report of Commissioned Test Results as to Fibersol-2H" issued by President of Nara Institute of Science and Technology, issued on Oct. 3, 2017, pp. 2-5, along with its English-language translation.

Hiroaki Hamano, "Properties and Application of Polydextrose", *Journal of Fiber Science and Technology*, vol. 48 (1992) No. 4, pp. 184-189, (with partial English language translation).

Noriko Hayashi et al., "Effects of Resistant Hydrogenated Starch Hydrolysate on Postprandial Blood Glucose Levels", *Journal of Japan Society of Nutrition and Food Sciences*, vol. 59 (2006) No. 5, pp. 247-253 (with partial English language translation).

Koji Katamune et al., "Retardation Phenomena of Levoglucosan on the Hardening of "Shiratama-ko" Gels", *Journal of Applied Glycoscience*, vol. 47 (2000) No. 3-4, pp. 327-333 (with partial English language translation).

Extended European Search Report dated Feb. 19, 2016 for corresponding EP Application No. 15730682.0.

International Search Report/ Written Opinion dated Apr. 14, 2015 for PCT/JP2015/050525.

Zhong Xu et al., "Functionally Modified Starch," China Light Industry Press, Apr. 2010, pp. 71-73.

"Chemical Basis of the Origin of Life," edited by Harada Xin, translated by Zhencheng Geng, Shanghai Science and Technology Press, Apr. 1978, pp. 151-154.

Second Office Action dated Oct. 30, 2020 in Chinese Application No. 201580065552.3.

DIETARY FIBER

This application is the National Stage of International Application No. PCT/JP2015/050525, filed Jan. 9, 2015, and claims benefit of Japanese Application No. 2014-266551 filed on Dec. 26, 2014.

TECHNICAL FIELD

The present invention relates to a dietary fiber in which the ratio of aldoses present as terminal sugars is largely reduced, in particular, a specific dietary fiber in which the ratio of anhydrosugars and/or sugar alcohols present as terminal sugars is high, and a method for producing such a dietary fiber.

In addition, the present invention relates to a dietary fiber-based material and a food item each comprising such a dietary fiber.

BACKGROUND ART

It is usually claimed that fiber intake has been reduced along with the change and diversification in dietary habits. In an attempt to increase dietary fiber intake, an indigestible dextrin was developed by improvement of pyrodextrins, which had never been expected to be used as a dietary fiber due to their pungent smell etc. (Patent Literature 1).

Furthermore, an improved indigestible dextrin with a reduced amount of colored substances and a reduced pungent smell is also known, and such improvements can be done by increasing the indigestible fraction content and the dietary fiber content (Patent Literature 2). Specifically, this novel indigestible dextrin contains 90% or more of indigestible components and 20% or more of dietary fibers relative to the components other than glucose, and can be obtained by hydrolyzing pyrodextrins with α-amylase and glucoamylase, and separating and removing the digestible fraction by ion-exchange resin chromatography.

As a dietary fiber other than indigestible dextrin, for example, polydextrose is also known, which was created in a new food material development project aiming to provide safe, easy-to-use and low-calorie food materials (Non Patent Literature 1). Polydextrose is a polyglucose and is synthesized, for example, from a mixture of about 89% of dextrose, 10% of sorbitol and 1% of citric acid (Patent Literature 3).

Polydextrose has a slightly bitter taste and for this reason, its application to foods has been limited. The bitterness of polydextrose is attributed to the presence of anhydroglucose, and it is known that the color and anhydroglucose content of polydextrose can be reduced by addition of a specific solvent (s) and treatment with a bleaching agent approved for use in foods (Patent Literature 4).

Anhydroglucose ((β-1,6-anhydroglucose) is also called levoglucosan and is a kind of sugar widely present in food materials such as polydextrose (Non Patent Literature 2). For example, the anhydroglucose content of polydextrose is known to be generally less than about 4% (Non Patent Literature 1). In addition, levoglucosan is known to be effective for slow solidification of starch gels (Non Patent Literature 2).

CITATION LIST

Patent Literature

Patent Literature 1: JP 4-43624 B2
Patent Literature 2: JP 6-32802 A
Patent Literature 3: U.S. Pat. No. 3,876,794
Patent Literature 4: U.S. Pat. No. 4,622,233

Non Patent Literature

Non Patent Literature 1:
Fiber, vol. 48, No. 4, 184-189 (1992)
Non Patent Literature 2:
J. Appl. Glycosci., vol. 47, No. 3&4, 327-333 (2000)

SUMMARY OF INVENTION

Technical Problem

As mentioned above, the problems in the use of dietary fibers include pungent smell and undesirable coloring, and strenuous efforts for improvement have been made so far.

However, currently available dietary fibers still have a distinctive bitterness and an unpleasant aftertaste. Therefore, the development of dietary fibers which do not adversely affect the good taste of food is desired.

The present invention has been made in order to solve the above-mentioned problems and is intended to provide an improved dietary fiber having less adverse effects on the taste of food, and to also provide a method for producing the improved dietary fiber.

In addition, the present invention is intended to provide a dietary fiber-containing food item which retains its original good taste.

Solution to Problem

The present inventors conducted intensive research to solve the above-mentioned problems. The present inventors focused on the terminal sugars of polysaccharides constituting a dietary fiber, and investigated the relation between the terminal sugars and the taste of the dietary fiber. After much trial and error, the present inventors obtained the following findings: surprisingly, the bitterness and unpleasant aftertaste of dietary fibers can be restrained by reducing the amount of aldehyde groups in the terminal sugars; and a dietary fiber obtained in the above manner has an improved taste (flavor and taste), and even when blended with food, does not disturb the original good taste (flavor and taste) of the food. Based on the findings, the present inventors completed the present invention.

Generally in a polymer of glucose, a terminal glucose in which the carbon atom at position 1 (C1) is at the molecular terminal has reducing properties and is often called a reducing terminal. In contrast, sugars without any aldehyde group do not have reducing properties. In this specification, a terminal sugar residue in which C1 is at the molecular terminal of a sugar chain is referred to simply as a "terminal sugar", and a functional group containing C1 of the terminal sugar is referred to as a "terminal functional group." In the dietary fiber of the present invention, the terminal sugars include an aldose and sugar derivatives such as an anhydrosugar and a sugar alcohol. The aldose can have a cyclic or straight-chain structure, and both a cyclic hemiacetal structure and a straight-chain aldehyde structure are present at equilibrium.

That is, the dietary fiber of the present invention has terminal sugars (terminal groups) (or consists of polysaccharides having a terminal sugar) and is characterized in that the ratio of aldoses relative to the total of the terminal sugars is 10% or less (for example, 4% or less).

The dietary fiber of the present invention may have, in particular, anhydrosugars and/or sugar alcohols as terminal sugars not having any aldehyde group. Such a dietary fiber may be, for example, the one for which the value of the following (A) is 0.1 or less (0 to 0.1).

$$(A)=X/(X+Y+Z)$$

(In the formula, X represents the number of sugar chains in which the terminal sugar is an aldose (or the number of aldoses relative to the total of the terminal sugars), Y represents the number of sugar chains in which the terminal sugar is an anhydrosugar (or the number of anhydrosugars relative to the total of the terminal sugars), and Z represents the number of sugar chains in which the terminal sugar is a sugar alcohol (or the number of sugar alcohols relative to the total of the terminal sugars).)

In addition, the above-described dietary fiber may be the one for which the value(s) of the following (B) and/or (C) is 0.6 to 1.

$$(B)=Y/(X+Y)$$

$$(C)=Z/(X+Z)$$

(In the formulae, X, Y and Z are as defined above.)

The dietary fiber of the present invention may be indigestible dextrin or polydextrose (in other words, a dietary fiber produced from indigestible dextrin or polydextrose as a raw material).

The indigestible dextrin may be, for example, a dietary fiber for which the value(s) of the above (B) and/or (c) is 0.8 to 1, and in particular, a dietary fiber for which the value of the above (B) is 0.9 to 1.

Typical examples of the indigestible dextrin include a dietary fiber for which the value of the above (A) is 0 to 0.04, the value of the above (B) is 0.95 to 1, and the value of the above (C) is 0.95 to 1.

The polydextrose may be, for example, a dietary fiber for which the value of the above (B) is 0.6 to 1 (for example, 0.7 to 1). Typical examples of the polydextrose include a dietary fiber for which the value of the above (A) is 0 to 0.04, the value of the above (B) is 0.75 to 1, and the value of the above (C) is 0.9 to 1.

The present invention includes a dietary fiber-based material comprising the above-described dietary fiber. The dietary fiber-based material comprises the above-described dietary fiber as a dietary fiber (dietary fiber component). The dietary fiber-based material may comprise, for example, 90% by weight or more (for example, 96% by weight or more) of the above-described dietary fiber relative to the total of dietary fibers having terminal sugars. The above-described dietary fiber in the dietary fiber-based material may be, for example, indigestible dextrin and/or polydextrose, and in particular, indigestible dextrin.

The dietary fiber of the present invention has a restrained bitterness and thus is a useful dietary fiber as a supplementary ingredient for food. The present invention therefore includes a food additive (for example, a beverage additive (e.g. an additive for alcoholic beverages)) which is composed of the above-described dietary fiber (or dietary fiber-based material).

The dietary fiber and the dietary fiber-based material of the present invention can be produced from, for example, a dietary fiber or a dietary fiber-based material each having reducing terminals. A typical method for producing the dietary fiber and the dietary fiber-based material of the present invention may be a method in which a dietary fiber or a dietary fiber-based material (indigestible dextrin, polydextrose, etc.) each having aldoses as terminal sugars is subjected to at least one treatment selected from reducing treatment, heat treatment and acid treatment.

The present invention also includes a food item comprising the dietary fiber or the dietary fiber-based material. The food item may comprise 1% by weight or more (for example, 2% by weight or more) of the dietary fiber or the dietary fiber-based material.

The food item may be a beverage. The beverage may be an alcoholic beverage (for example, a beverage with an alcohol content of 1% or more) or a beverage containing carbon dioxide gas (carbonated beverage). In particular, the beverage may be a malt fermented beverage (beer etc.). In addition, the beverage may be a whiskey (for example, bourbon whisky), in particular a highball (whiskey-containing carbonated beverage).

Advantageous Effects of Invention

According to the present invention, an improved dietary fiber which has less adverse effects on the taste of food (for example, less unpleasant aftertaste, specifically less bitterness) due to the reduced ratio of aldoses present as terminal sugars, and a method for producing the improved dietary fiber can be provided.

In addition, with use of such a dietary fiber, a dietary fiber-containing food item which retains its original good taste can be provided.

DESCRIPTION OF EMBODIMENTS

<Dietary Fiber>

The dietary fiber which can be used in the present invention is a glucose polymer-based dietary fiber. For example, indigestible dextrin, polydextrose, β-glucan, mannan, pectin, etc. are included. In addition, cellulose, which is a polymer of β-glucose, and hemicellulose are also included.

Among these, indigestible dextrin and polydextrose are particularly preferred.

In general, the definition of dietary fibers has not been standardized yet, and hence, in a strict sense, there is no method for quantitative determination of dietary fibers.

The dietary fiber in the present invention can be quantified by the high-performance liquid chromatography (HPLC) or the Prosky method specified in the "Nutrition Labelling Standards (the Public Notice of the Ministry of Health, Labour and Welfare No. 176 (2003))".

The dietary fiber used may be of one kind or any combination of two or more kinds.

The dietary fiber (polysaccharides) of the present invention has a low ratio of aldoses present as terminal sugars, as mentioned above. For example, the ratio of aldoses relative to the total of the terminal sugars in the dietary fiber of the present invention can be about 20% or less (for example, about 15% or less), and may be usually 10% or less (for example, 7% or less), preferably 5% or less, more preferably 4% or less, and in particular 3% or less (for example 2% or less, preferably 1% or less).

The ratio of aldoses in the terminal sugars of the dietary fiber of the present invention is decreased as described above. This is achieved by conversion of terminal aldoses into different structures (or different terminal sugars) by chemical modification etc. The structures different from aldose are not particularly limited, but particularly preferred are an anhydrosugar (for example, 1,6-anhydrosugar) structure, and a sugar alcohol (or alcohol) structure.

The anhydrosugar is a dehydrated product of a sugar and has an ether bond formed by dehydration between two hydroxyl groups (for example, a hemiacetal hydroxyl group and another hydroxyl group) of the sugar. For example, glucose is known to be transformed into β-1,6-anhydrosugar (levoglucosan) by intramolecular dehydration condensation of the C1 hydroxyl group and the C6 hydroxyl group, which are spatially close to each other in terms of the steric configuration. The anhydrosugar can be formed by heat treatment, acid treatment, etc. as described later.

The sugar alcohol can be formed by, for example, reduction of the terminal aldehyde group. In the case where the terminal sugar is glucose, sorbitol is formed by such a reduction.

Therefore, the terminal sugars of the dietary fiber may mainly include an aldose, an anhydrosugar and a sugar alcohol.

Specifically, for the dietary fiber of the present invention, the value of the following (A), which is a measure of the ratio of aldoses present as terminal sugars, may be for example 0 to 0.2 (for example, 0 to 0.15), preferably 0 to 0.1 (for example, 0 to 0.07), more preferably 0 to 0.05, in particular 0 to 0.04, and particularly preferably 0 to 0.03 (for example 0 to 0.02, preferably 0 to 0.01).

$$(A)=X/(X+Y+Z)$$

(In the formula, X represents the number of sugar chains in which the terminal sugar is an aldose, Y represents the number of sugar chains in which the terminal sugar is an anhydrosugar, and Z represents the number of sugar chains in which the terminal sugar is a sugar alcohol.)

X can be said to be the number of aldoses relative to the total of the terminal sugars. Similarly, Y can be said to be the number of anhydrosugars relative to the total of the terminal sugars, and Z can also be said to be the number of sugar alcohols relative to the total of the terminal sugars.

For the dietary fiber of the present invention, the value of the following (A'), which is a measure of the ratio of anhydrosugars and/or sugar alcohols present as terminal sugars, may be for example 0.8 to 1 (for example, 0.85 to 1), preferably 0.9 to 1 (for example, 0.93 to 1), more preferably 0.95 to 1, in particular 0.96 to 1, and particularly preferably 0.97 to 1 (for example 0.98 to 1, preferably 0.99 to 1).

$$(A')=(Y+Z)/(X+Y+Z)$$

(In the formulae, X, Y and Z are as defined above.)

For the dietary fiber of the present invention, the value of the following (B), which is a measure of the ratio of anhydrosugars to aldoses present as terminal sugars, may be for example 0.5 to 1, preferably 0.6 to 1 (for example, 0.65 to 1), more preferably 0.7 to 1, and in particular 0.8 to 1.

$$(B)=Y/(X+Y)$$

(In the formulae, X and Y are as defined above.)

The value of the above (B) may be adjusted as appropriate depending on the kind of the dietary fiber. For example, the value of (B) for indigestible dextrin may be 0.8 to 1, preferably 0.9 to 1, and more preferably 0.95 to 1.

The value of (B) for polydextrose may be in particular 0.6 to 1 (for example, 0.65 to 0.99), preferably 0.7 to 1 (for example, 0.7 to 0.95), and more preferably 0.75 to 1 (for example, 0.75 to 0.9).

For the dietary fiber of the present invention, the value of the following (C), which is a measure of the ratio of sugar alcohols to aldoses present as terminal sugars, may be for example 0.5 to 1, preferably 0.6 to 1 (for example, 0.65 to 1), more preferably 0.7 to 1, and in particular 0.8 to 1.

$$(C)=Z/(X+Z)$$

(In the formulae, X and Z are as defined above.)

The value of the above (C) may be adjusted as appropriate depending on the kind of the dietary fiber. For example, the value of (B) for indigestible dextrin or polydextrose may be 0.8 to 1, preferably 0.9 to 1, and more preferably 0.95 to 1.

<Dietary Fiber-Based Material>

The present invention also includes a dietary fiber-based material comprising the above-described dietary fiber.

The dietary fiber-based material is not particularly limited as long as it comprises the above-described dietary fiber, but preferred is for example a dietary fiber-based material in which the dietary fiber content (or indigestible fraction content) is 70% by weight or more relative to the solid content (excluding water) by weight. A higher dietary fiber content of the dietary fiber-based material is more desirable. For example, the dietary fiber content is preferably 75% by weight or more, and more preferably 80% by weight or more.

The dietary fiber content of the dietary fiber-based material is expressed as the weight percentage (%) of the dietary fiber relative to the weight of the total solids (excluding water), and the water content is not particularly taken into consideration. That is, for example, in the case where a dietary fiber-based material with a water content of 10% by weight has a dietary fiber content of 90% by weight in a dried powder form, the actual weight ratio of the dietary fiber to the total weight of the material is 81% by weight, but in this description, the dietary fiber content is described as 90% by weight.

The dietary fibers which constitute the dietary fiber-based material have to contain a dietary fiber having terminal sugars, but may contain other dietary fibers (for example, non-polysaccharide dietary fibers (lignin etc.).

In the dietary fiber-based material of the present invention, the ratio of the above-described dietary fiber (a dietary fiber with a low ratio of aldoses present as terminal sugars) relative to the total of dietary fibers having terminal sugars can be about 75% by weight or more (for example, 80% by weight or more), may be usually 85% by weight or more (for example, 90% by weight or more), more preferably 95% by weight or more (for example, 96% by weight or more), in particular 97% by weight or more (for example, 98% by weight or more), and may be 100% by weight.

The dietary fiber-based material is not subject to any limitation on its form and may be in a solid or liquid form, but preferred is a powder form in view of ease of measuring and dispensing, water solubility and storage stability. The water content in the powder form is set to preferably 15% by weight or less, and more preferably 10% by weight or less in view of storage stability. However, in the case where there is no need for special attention to storage stability, for example, there is no intention of long-term storage, a liquid form can be preferably used without any particular problem. The water content in the liquid form is not particularly limited, but is preferably 20 to 40% by weight, for example.

<Method for Producing Dietary Fiber>

The method for producing the dietary fiber of the present invention is not particularly limited as long as the method can reduce the amount of aldehyde groups in the reducing terminals.

The dietary fiber of the present invention can be obtained by performing a treatment for removal or conversion (change) of aldehyde groups in the course of a production process of dietary fibers from carbohydrates. Alternatively, a dietary fiber having aldoses as terminal sugars may be subjected to a treatment for removal or conversion (change) of aldehyde groups for production of the dietary fiber of the present invention.

For example, by performing heat or acid treatment under specific conditions in the production of dietary fibers, a reducing terminal can be converted into an anhydrosugar. That is, heat or acid treatment promotes etherification of the reducing terminal through dehydration between two hydroxyl groups, resulting in the formation of an anhydrosugar.

In the case where dietary fibers partially containing a dietary fiber with a low ratio of aldoses present as terminal sugars (that is, the dietary fiber of the present invention) can be obtained in the production process, the dietary fiber with a low ratio of aldoses present as terminal sugars can be processed into the dietary fiber of the present invention.

Examples of such processing include separation treatment (preparative separation, and separation by fractionation), reducing treatment, heat treatment and acid treatment. These treatments may be employed alone or in a combination of two or more kinds.

The separation treatment can be selected as appropriate depending on the difference in chemical species of the terminal sugar, i.e., the chemical difference between an aldose and other terminal sugars (a sugar alcohol, an anhydrosugar, etc.). For example, an ion-exchange resin (ion-exchanger) may be used for separation of the dietary fiber of the present invention from a mixture of the dietary fiber of the present invention and other dietary fibers (dietary fiber mixture).

The ion-exchange resin includes a cation-exchange resin and an anion-exchange resin. Examples of the cation-exchange resin include Dowex 50WX8 (manufactured by the Dow Chemical Company), and DIAION (registered trademark) series UBK8, UBK10 and UBK12 (manufactured by Mitsubishi Chemical Corporation). Examples of the anion-exchange resin include DIAION UBA120 (manufactured by Mitsubishi Chemical Corporation), and Dowex 1X8, Dowex 22 and Dowex 66 (manufactured by the Dow Chemical Company).

The reducing treatment can convert an aldehyde group into an alcohol group (an aldose into a sugar alcohol). Specific examples of the reducing treatment include a method using a reducing agent such as $NaBH_4$ and $LiAlH_4$; and a method using hydrogen as a reducing agent in the presence of a catalyst such as nickel, ruthenium, palladium and platinum. These methods are known to the skilled person and both may be used in the present invention.

The heat or acid treatment of a dietary fiber can convert a reducing terminal into an anhydrosugar.

<Method for Quantifying Terminal Sugars of Dietary Fibers>

The method for quantifying the terminal sugars of dietary fibers is not particularly limited, and for example, such quantification can be preferably performed by using a mass spectrometer etc. as a detector. The mass spectrometer is not particularly limited as long as it is suitable for ionization of dietary fibers and detection of the product ions. In the present invention, the mass spectrometer may be sometimes called an MS detector.

For example, a dietary fiber having a sugar alcohol as the terminal sugar has a larger molecular weight by the mass of two hydrogen atoms (that is, by 2) than that of a dietary fiber having an aldose as the terminal sugar. A dietary fiber having an anhydrosugar as the terminal sugar has a smaller molecular weight by the mass of one water molecule (that is, by 18) than that of a dietary fiber having an aldose as the terminal sugar.

This difference in molecular weight can be revealed by using an MS detector. Hence, the ratio of the numbers of molecules of these different dietary fibers can be determined by calculating the ratio of the mass spectral peak height or area of a dietary fiber having a sugar alcohol or an anhydrosugar as the terminal sugar relative to that of a dietary fiber having an aldose as the terminal sugar. In this case, it is preferable to compare the peaks in the same degree of polymerization because the ionizability of a dietary fiber is somewhat variable with its molecular weight.

For the quantification of the terminal sugars, all or a part of the dietary fibers may be used. When a part of the dietary fibers are used for quantification, it is optional and preferable that the dietary fibers used therefor are selected based on their MS detectability, etc.

<Application of Dietary Fiber>

Optionally and preferably, the dietary fiber of the present invention is used as in particular a supplementary ingredient for food. The dietary fiber of the present has a restrained bitterness and thus can be added to food without impairing the taste of the food. Therefore, the dietary fiber of the present invention can be used in particular as a food additive.

The effect of the present invention is to reduce the bitter taste, unpleasant aftertaste, stimulating sensation, irritation of some kind and unpleasant flavor of dietary fibers. In describing the taste and flavor of dietary fibers, for example, "having a pungent smell and an unpleasant flavor" (Patent Literature 1), and "having a slightly bitter taste" (Patent Literature 3) are used. Such a difference in descriptions can be partly attributed to the concentration of dietary fibers in food. For example, it is easily imaginable that a slightly bitter taste of dietary fibers is recognized as an unpleasant aftertaste or associated with stimulating sensation etc., and thus described as an unpleasant flavor. In the present invention, the bitter taste, unpleasant aftertaste, stimulating sensation, unpleasant flavor, etc. of dietary fibers may be collectively described as bitterness. That is, the effect of the present invention can be described as the reduction of the bitterness of dietary fibers.

Further, the present invention includes a composition comprising the above-described dietary fiber. Such a composition can be used as a food item (food and beverage item), a pharmaceutical product, a quasi drug, etc.

Examples of the food item (food and beverage item) include foods, beverages, seasonings, functional foods (foods with health-promoting benefits), health foods, nutritional supplementary foods, foods for specified health use and supplements.

The foods may be frozen foods, chilled foods, retort pouch foods, instant foods or the like. In addition, the foods may be the ones that can be prepared just before use (for example, powders to be dissolved in coffee, tea, juice, yogurt, soup, etc.; powders to be mixed with ingredients for cooking; etc.).

The beverages may be dairy beverages, alcoholic beverages, carbonated beverages or the like.

Specific examples of the foods include rice dishes, noodles (fresh noodles, dried noodles, instant noodles, etc.), bread, other flour-based products, curry roux, stew roux, dairy products (ice cream etc.), processed dairy products, milk, soft drinks, carbonated beverages, green tea, black tea, oolong tea, coffee, cocoa, refined sake, beer, low-malt beer, synthetic sake, sweet cooking sake, wine, shochu (distilled spirit), whiskey, vegetable juice, seasonings (miso (fermented soybean paste), soy sauce, vinegar, umami seasoning, dressing, sauce, mayonnaise, etc.), processed fishery products (fish paste, fish ham, fish sausage, dried bonito, preserved foods boiled in sweetened soy sauce, etc.), croquette, hamburg steak, shumai (steamed meat dumpling), gyoza (meat and vegetable dumpling), gratin, instant soup, instant curry, instant miso soup, instant coffee, and confectioneries (Japanese-style confectionery, Japanese-style wet confectionery, Japanese-style half-wet confectionery, Western-style confectionery, Western-style wet confectionery, Western-style half-wet confectionery, hard candies, chocolate, chewing gums, jellies, biscuits, rice confectionery, snacks, fried confectionery, cheap confectionery, etc.).

The dietary fiber of the present invention is not affected by alcohol or carbon dioxide gas, and thus may be added to an alcoholic beverage (alcohol-containing beverage) or a carbonated beverage (carbon dioxide gas-containing beverage) among others. The alcoholic beverage may be carbonated. Hereinafter, the alcoholic beverage will be explained in more detail.

<Alcoholic Beverage>

In this specification, "alcohol" means ethyl alcohol (ethanol) unless otherwise stated. "Alcohol content" means the volume percentage (%) of the alcohol in an aqueous alcoholic solution.

The alcohol that can be used in the present invention is not particularly limited. Examples of the alcohol include brewing alcohol; spirits (for example, spirits such as gin, vodka, rum, tequila and new spirits, material alcohol, etc.); liqueurs; whiskeys (for example, bourbon whiskey, Scotch whisky, highballs (whiskey highballs), etc.); brandies; and shochu (multiple-distilled shochu (also called Korui shochu) and single-distilled shochu (also called Otsurui shochu)). Other examples are brewed beverages (refined sake, wines, malt fermented beverages (beers etc.), makgoli, etc.).

The alcohol concentration in the alcoholic beverage is not particularly limited. However, the dietary fiber of the present invention is preferably used in so-called low-alcohol beverages because the reduced bitterness and easy intake of the dietary fiber is highly advantageous in such beverages. The alcohol content is preferably 10 v/v % or less for an advantageous effect of the present invention. More preferred is 8 v/v % or less, and still more preferred is 5 v/v % or less. Even when the alcohol content exceeds 10 v/v %, it causes no particular problems for the effect of the present invention, but alcoholic beverages with such a high alcohol content may be unsuitable as a beverage for convenient intake of dietary fibers. The lower limit of the alcohol content is not particularly set, but in a preferable embodiment, the alcohol content is 1 v/v % or more.

The alcohol-containing beverage in the present invention can contain carbon dioxide gas (that is, can be carbonated). The pressure of the carbon dioxide gas in the carbon dioxide gas-containing beverage of the present invention is preferably such a level that the carbon dioxide gas-containing beverage gives a refreshing feeling when consumed. Specifically, the suitable pressure of the carbon dioxide gas is 0.5 to 3.0 kgf/cm$^2$, and more preferably 1.5 to 3.0 kgf/cm$^2$ as measured by a method usually known to the skilled person.

The percentage of the dietary fiber of the present invention blended in a composition (food item etc.) is not particularly limited as long as the dietary fiber does not disturb the original good taste of food. For example, when the dietary fiber of the present invention is blended with a bland food, the effect of the present invention can be exerted at a percentage of 0.1% by weight or more, but the percentage of the dietary fiber may be preferably 0.5% by weight or more, more preferably 1% by weight or more (for example, 1.5 to 50% by weight), and most preferably 2% by weight or more (for example, 2 to 30% by weight or more). Generally, a dietary fiber blended at a higher percentage with food has a greater influence on the original good taste of the food. However, at such a higher percentage, the present invention is more advantageous. In particular, when the dietary fiber of the present invention is blended with a beverage (an alcoholic beverage etc.) or the like, the effect of the present invention can be exerted at a percentage of 0.1% by weight or more, but for example, the percentage of the dietary fiber may be 1% by weight or more (for example, 1.5 to 20% by weight), and preferably 2% by weight or more (for example, 2 to 10% by weight).

EXAMPLES

Hereinafter, the present invention will be illustrated in more detail by Examples below, but is not limited thereto.

Production Example 1

Production of Indigestible Dextrin in which Terminal Sugar is Sugar Alcohol

Twenty grams of a commercial indigestible dextrin (NUTRIOSE (registered trademark) FM manufactured by Roquette: the dietary fiber content measured by the Prosky method was 91%) was weighed out and dissolved in 200 ml of Milli-Q water, 10 g of NaBH$_4$ was added, and the mixture was left to stand at room temperature for 16 hours. By addition of an appropriate amount of acetic acid, bubbling was made to stop and the pH was made to about 2. The produced boric acid and sodium acetate were removed using ion-exchange resins. The anion-exchange resin used was Amberlite IRA-400 (OH$^-$ form) (manufactured by the Dow Chemical Company), and the cation-exchange resin used was Amberlite IR-120 (H$^+$ form) (manufactured by the Dow Chemical Company). To be more specific, the reaction mixture was first passed through the cation-exchange resin at a pH of 2, elution was performed with Milli-Q water, the obtained dietary fiber-containing fraction was passed through the anion-exchange resin, and elution was performed with Milli-Q water. The eluate was concentrated in an evaporator and dried in a freeze dryer to give about 12 g of a dietary fiber-based material powder (test sample A).

Test sample A was further purified with the ion-exchange resins to prepare test sample B. That is, the aqueous solution obtained before the concentration and drying step in the production procedure of test sample A was subjected to adsorption on the cation-exchange resin and subsequent elution with Milli-Q water, the desired fraction was subjected to adsorption on the anion-exchange resin and subsequent elution with Milli-Q water, and this series of steps was repeated until the eluate became neutral (pH=7). The eluate was finally concentrated in an evaporator and dried in a freeze dryer to give about 11 g of a dietary fiber-based material powder (test sample B).

Production Example 2

Production of Indigestible Dextrin in which Terminal Sugar is Anhydrosugar

Twenty grams of a commercial indigestible dextrin (NUTRIOSE FM manufactured by Roquette: the dietary fiber content measured by the Prosky method was 91%) was weighed out and dissolved in 200 ml of Milli-Q water. The solution was passed through the anion-exchange resin and elution was performed with Milli-Q water. The obtained dietary fiber-containing fraction was further passed through the anion-exchange resin, and elution was performed with Milli-Q water. The eluate was passed through the cation-exchange resin, and the resulting eluate was concentrated in an evaporator and dried in a freeze dryer to give about 7.5 g of a dietary fiber-based material powder (test sample C).

Production Example 3

Production of Polydextrose in which Terminal Sugar is Anhydrosugar

Twenty grams of polydextrose (Litesse (registered) trademark) II manufactured by Du Pont: the dietary fiber content measured by the Prosky method was 82%) was weighed out and dissolved in 200 ml of Milli-Q water. The solution was passed through the anion-exchange resin, and elution was performed with Milli-Q water. The first half portion of the eluate and the latter half portion of the eluate were separately pooled. The first half portion of the eluate was passed through the cation-exchange resin, and the resulting eluate was concentrated in an evaporator and dried in a freeze dryer to give about 7.6 g of a dietary fiber-based material powder (test sample D).

The latter half portion of the eluate was directly concentrated in an evaporator and dried in a freeze dryer to give about 4.6 g of a dietary fiber-based material powder (test sample E).

<Identification of Terminal Sugars of Dietary Fibers in Dietary Fiber-Based Materials>

The dietary fibers in the dietary fiber-based materials obtained in Production Examples 1 to 3 (test samples A to E) and commercial dietary fiber-based materials (reference products A to E) were analyzed, and aldoses, anhydrosugars and sugar alcohols as the terminal sugars were quantified.

The reference products A to E are as follows.
Reference product A: Indigestible dextrin (NUTRIOSE FB manufactured by Roquette: the dietary fiber content measured by the Prosky method was 91%)
Reference product B: Indigestible dextrin (NUTRIOSE FM manufactured by Roquette: the dietary fiber content measured by the Prosky method was 91%; this was used as the starting material in Production Examples 1 and 2)
Reference product C: Indigestible dextrin (E-fiber manufactured by Matsutani Chemical Industry Co., Ltd.: the dietary fiber content measured by the Prosky method was 92%)
Reference product D: Polydextrose (Litesse II manufactured by Du Pont: the dietary fiber content measured by the Prosky method was 82%; this was used in Production Example 3)
Reference product E: Polydextrose (WINWAY ACME manufactured by Shanghai Winway Dietary Fiber Development Co., Ltd.: the dietary fiber content measured by the Prosky method was 88%)

The terminal sugars of reference product D were quantified in the following manner.

The mass analysis of reference product D was performed by matrix-assisted laser desorption/ionization time-of-flight mass spectrometry (MALDI-TOF MS), which is suitable for analysis of dietary fibers such as sugar polymers.

For preparation of a dietary fiber solution, 10 mg of the dietary fiber was weighed out and dissolved in 0.2 mL of Milli-Q water, and about 1 mg of sodium trifluoroacetate as an ionizing agent was added in order to produce sodium adduct ions as analyte ions. For preparation of a matrix solution, 30 mg of 2,5-dihydroxybenzoic acid (DHB), which can assist optimal ionization of dietary fiber-based materials, was dissolved in 1 mL of a mixed solvent of Milli-Q water/acetonitrile (1/1 v/v).

A one-microliter droplet of the dietary fiber solution was mixed with the same volume droplet of the matrix solution on a stainless steel plate for MALDI, and the mixture was dried in a vacuum dryer to prepare a mixed crystal as a measurement sample for MALDI. MS spectra were acquired using Ultraflex III MALDI-TOF/TOF MS (manufactured by Bruker Corporation). Each spectrum was generated by accumulating the data from 2000 or more laser shots. The fluence of the irradiation laser beam was appropriately adjusted so as to ensure acquisition of proper mass spectra, i.e., mass spectra with a signal-to-noise ratio of 50 or more and a resolution of 5000 or more.

In the resulting spectrum, three peaks were observed at m/z=995, 1013 and 1015. Considering that reference product D is a glucose polymer-based dietary fiber, the peak at m/z=1013 in the spectrum corresponds to a $[M+Na]^+$ ion with a degree of glucose polymerization of 5 (excluding glucose as the terminal sugar) and is indicative of the presence of a dietary fiber having an aldehyde group.

The peak at m/z=995 in the spectrum corresponds to a $[M-H_2O+Na]^+$ ion with a degree of glucose polymerization of 5 (excluding a terminal sugar) and is indicative of the presence of a dietary fiber having an anhydrosugar as the terminal sugar residue.

Figure 1:
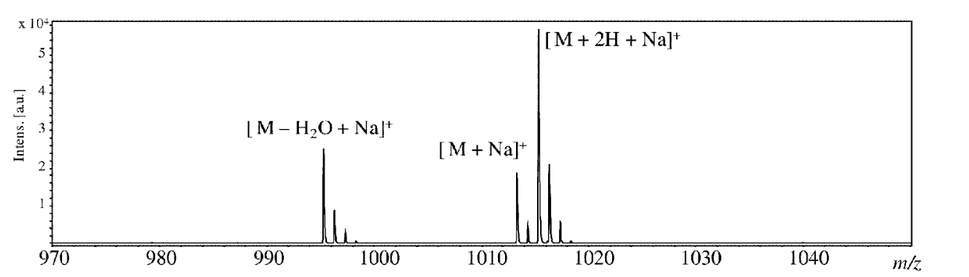
FIG. 1 is an enlarged view of the MS spectrum of reference product D in the m/z range of 970 to 1050.

The peak at m/z=1015 in the spectrum corresponds to a $[M+2H+Na]^+$ ion with a degree of glucose polymerization of 5 (excluding a terminal sugar) and is indicative of the presence of a dietary fiber having a sugar alcohol as the terminal sugar residue. The MS spectrum is shown in FIG. 1.

In the mass range (m/z range) of 990 to 1550, the same series of peaks was repeatedly observed for each of the following degrees of polymerization (excluding a terminal sugar): 5 (m/z=995, 1013, 1015), 6 (m/z=1157, 1175, 1177), 7 (m/z=1319, 1337, 1339), and 8 (m/z=1481, 1499, 1501). At each degree of polymerization, the monoisotopic peak heights of a dietary fiber having an aldose as the terminal sugar, a dietary fiber having an anhydrosugar as the terminal sugar, and a dietary fiber having a sugar alcohol as the terminal sugar were measured, and the respective ratios were calculated. The resulting values for each dietary fiber were averaged over all the degrees of polymerization to quantify each terminal sugar.

Similarly, the terminal sugars of test samples A to E and other reference products were quantified.

The obtained results are shown in the following table.

TABLE 1

| Dietary fiber-based material | Indigestible dextrin | | | | | | Polydextrose | | | |
|---|---|---|---|---|---|---|---|---|---|---|
| | Test sample A | Test sample B | Test sample C | Reference product A | Reference product B | Reference product C | Test sample D | Test sample E | Reference product D | Reference product E |
| X/(X + Y + Z) | 0.025 | 0.001 | 0.025 | 0.625 | 0.470 | 0.894 | 0.032 | 0.129 | 0.137 | 0.187 |
| (Y + Z)/(X + Y + Z) | 0.975 | 0.999 | 0.975 | 0.375 | 0.530 | 0.106 | 0.968 | 0.871 | 0.863 | 0.813 |
| Y/(X + Y) | 0.960 | 0.998 | 0.975 | 0.375 | 0.530 | 0.106 | 0.659 | 0.573 | 0.546 | 0.374 |
| Z/(X + Z) | 0.935 | 0.999 | 0.000 | 0.000 | 0.000 | 0.000 | 0.966 | 0.844 | 0.835 | 0.789 |

Examples 1

The flavors and tastes of test samples A to E and reference products A to E were rated by sensory evaluation of the respective aqueous solutions. The sensory evaluation focused on the bitterness and unpleasant aftertaste of dietary fibers, which are problems to be solved in the present invention.

Two hundred milligrams each of powdered test samples A to E and powdered reference products A to E were weighed out and separately dissolved in 10 ml of Milli-Q water. These 2% aqueous solutions were subjected to the sensory evaluation. In the sensory evaluation, five trained panelists rated the solutions on the following 4-point scale.
(Rating Criteria: Bitterness and Unpleasant Aftertaste)
  4: Bitterness and unpleasant aftertaste were not sensed.
  3: Bitterness and unpleasant aftertaste were hardly sensed.
  2: Bitterness and unpleasant aftertaste were sensed.
  1: Very intense bitterness and unpleasant aftertaste were sensed.

The results of the rating by the five panelists were averaged. When the average score is 1 or more and less than 2, the rating is represented as "poor"; when the average score is 2 or more and less than 3, the rating is represented as "fair"; and when the average score is 3 or more and 4 or less, the rating is represented as "good". The 3-point evaluation results were used as the final evaluation results.

The obtained evaluation results are as follows.

TABLE 2

| Dietary fiber-based material | Indigestible dextrin | | | | | | Polydextrose | | | |
|---|---|---|---|---|---|---|---|---|---|---|
| | Test sample A | Test sample B | Test sample C | Reference product A | Reference product B | Reference product C | Test sample D | Test sample E | Reference product D | Reference product E |
| X/(X + Y + Z) | 0.025 | 0.001 | 0.025 | 0.625 | 0.470 | 0.894 | 0.032 | 0.129 | 0.137 | 0.187 |
| (Y + Z)/(X + Y + Z) | 0.975 | 0.999 | 0.975 | 0.375 | 0.530 | 0.106 | 0.968 | 0.871 | 0.863 | 0.813 |
| Y/(X + Y) | 0.960 | 0.998 | 0.975 | 0.375 | 0.530 | 0.106 | 0.659 | 0.573 | 0.546 | 0.374 |
| Z/(X + Z) | 0.935 | 0.999 | 0.000 | 0.000 | 0.000 | 0.000 | 0.966 | 0.844 | 0.835 | 0.789 |
| Sensory evaluation | Good | Good | Good | Poor | Poor | Poor | Good | Poor | Poor | Poor |

The evaluation results were reviewed in the context of the analytical values (parameters) in relation to the terminal sugars.
<Parameters (A) and (A')>

The relation between parameter (A) (i.e., X/(X+Y+Z)) and the sensory evaluation, and the relation between parameter (A') (i.e., (Y+Z)/(X+Y+Z)) and the sensory evaluation are as shown in the above table.

Test samples A to D, which had a small value of parameter (A) (mostly 0.1 or less), were all rated as "good" in the sensory evaluation. However, test sample E and reference products A to E, which had a large value of parameter (A) (mostly more than 0.1), were all rated as "poor" (that is, bitterness and unpleasant aftertaste were sensed) in the sensory evaluation.

In the context of the value of parameter (A'), which is inversely correlated with that of parameter (A), the opposite tendency was observed (that is, at a smaller value of parameter (A'), more intense bitterness and unpleasant aftertaste were sensed).
<Parameters (B) and (C)>

The relation between parameter (B) (i.e., Y/(X+Y)) and the sensory evaluation, and the relation between parameter (C) (i.e., Z/(X+Z)) and the sensory evaluation are as shown in the above table.

The table shows that when the value of at least parameter (B) or (C) is large, the result of the sensory evaluation tends to be "good".

As shown above, parameter (A) or parameter (A'), and parameter (B) and/or (C) are related to the bitterness and unpleasant aftertaste of dietary fibers.

Example 2

Next shown is an example in which model carbonated beverages (alcohol concentration: about 8%) which mimicked whiskey highballs were experimentally produced and subjected to sensory evaluation. As is the case in Example 1, the sensory evaluation focused on the bitterness and unpleasant aftertaste of dietary fibers, which are problems to be solved in the present invention.

Five grams each of powdered test samples A to E and powdered reference products A to E were weighed out and separately well dissolved in a previously mixed solution of 50 ml of a commercial whiskey (Kakubin, manufactured by Suntory Holdings Limited) and 150 ml of a commercial carbonated water (manufactured by Suntory Holdings Limited), and the solution was made to 250 ml with the same carbonated water as above. These 2% aqueous model carbonated beverages were subjected to the sensory evaluation. The sensory evaluation was performed in the same manner as in Example 1.

The obtained evaluation results are as follows.

TABLE 3

| Dietary fiber-based material | Indigestible dextrin | | | | | | Polydextrose | | | |
|---|---|---|---|---|---|---|---|---|---|---|
| | Test sample A | Test sample B | Test sample C | Reference product A | Reference product B | Reference product C | Test sample D | Test sample E | Reference product D | Reference product E |
| $X/(X+Y+Z)$ | 0.025 | 0.001 | 0.025 | 0.625 | 0.470 | 0.894 | 0.032 | 0.129 | 0.137 | 0.187 |
| $(Y+Z)/(X+Y+Z)$ | 0.975 | 0.999 | 0.975 | 0.375 | 0.530 | 0.106 | 0.968 | 0.871 | 0.863 | 0.813 |
| $Y/(X+Y)$ | 0.960 | 0.998 | 0.975 | 0.375 | 0.530 | 0.106 | 0.659 | 0.573 | 0.546 | 0.374 |
| $Z/(X+Z)$ | 0.935 | 0.999 | 0.000 | 0.000 | 0.000 | 0.000 | 0.966 | 0.844 | 0.835 | 0.789 |
| Sensory evaluation | Good | Good | Good | Poor | Poor | Poor | Good | Poor | Poor | Poor |

As is clear from the above evaluation results, the ratings of the model carbonated beverages which mimicked whiskey highballs show the same pattern as those in Example 1, in which water was used.

This indicates that whatever the dietary fibers were added to, the relation between the terminal sugars of the dietary fibers and their bitterness and unpleasant aftertaste tends to be the same.

INDUSTRIAL APPLICABILITY

The dietary fiber (dietary fiber-based material) of the present invention has a restrained or reduced bitterness, and thus is a useful dietary fiber as a supplementary ingredient for food (food additive) etc.

The invention claimed is:

1. A dietary fiber having terminal sugars, wherein the terminal sugars comprise an anhydrosugar, wherein the ratio of aldoses relative to the total of the terminal sugars is 10% or less, and wherein the value of the following (B) is 0.6 to 0.998:

$$(B)=Y/(X+Y)$$

wherein X represents the number of sugar chains in which the terminal sugar is an aldose, and Y represents the number of sugar chains in which the terminal sugar is an anhydrosugar.

2. The dietary fiber according to claim 1, wherein the ratio of aldoses relative to the total of the terminal sugars is 4% or less.

3. The dietary fiber according to claim 1, wherein the value of the following (C) is 0.6 to 0.999:

$$(C)=Z/(X+Z), \text{ or}$$

wherein the value of the following (A) is 0.001 to 0.1:

$$(A)=X/(X+Y+Z)$$

wherein X represents the number of sugar chains in which the terminal sugar is an aldose, Y represents the number of sugar chains in which the terminal sugar is an anhydrosugar, and Z represents the number of sugar chains in which the terminal sugar is a sugar alcohol.

4. The dietary fiber according to claim 1, wherein the dietary fiber is indigestible dextrin or polydextrose.

5. The dietary fiber according to claim 3, wherein the dietary fiber is indigestible dextrin, and the value of the above (B) is 0.8 to 0.998, or the value of the above (C) is 0.8 to 0.999.

6. The dietary fiber according to claim 1, wherein the dietary fiber is indigestible dextrin and the value of the above (B) is 0.9 to 0.998.

7. The dietary fiber according to claim 3, wherein the dietary fiber is indigestible dextrin, the value of the above (A) is 0.001 to 0.04, the value of the above (B) is 0.95 to 0.998, and the value of the above (C) is 0.95 to 0.999.

8. The dietary fiber according to claim 1, wherein the dietary fiber is polydextrose.

9. The dietary fiber according to claim 1, wherein the dietary fiber is polydextrose and the value of the above (B) is 0.7 to 0.998.

10. The dietary fiber according to claim 3, wherein the dietary fiber is polydextrose, the value of the above (A) is 0.001 to 0.04, the value of the above (B) is 0.75 to 0.998, and the value of the above (C) is 0.9 to 0.999.

11. A dietary fiber-based material comprising the dietary fiber according to claim 1 in an amount of 90% by weight or more relative to the total of dietary fibers having terminal sugars.

12. The dietary fiber-based material according to claim 11, wherein the dietary fiber having terminal sugars, wherein the ratio of aldoses relative to the total of terminal sugars is 10% or less, is present in an amount of 96% by weight or more relative to the total of dietary fibers having terminal sugars.

13. The dietary fiber-based material according to claim 11, wherein the dietary fiber is indigestible dextrin.

14. A food additive composed of the dietary fiber or the dietary fiber-based material according to claim 1.

15. A food item comprising the dietary fiber or the dietary fiber-based material according to claim 1.

16. The food item according to claim 15, wherein the dietary fiber or the dietary fiber-based material is present in an amount of 1% by weight or more.

17. The food item according to claim 15, wherein the dietary fiber or the dietary fiber-based material is present in an amount of 2% by weight or more.

18. The food item according to claim 15, wherein the food item is a beverage.

19. The food item according to claim 15, wherein the food item is a beverage with an alcohol content of 1% or more.

20. The food item according to claim 15, wherein the food item is a carbonated beverage.

21. The food item according to claim 15, wherein the food item is a malt fermented beverage.

22. The food item according to claim 15, wherein the food item is a whiskey.

23. The food item according to claim 15, wherein the food item is a highball.

24. The dietary fiber according to claim 1, wherein the ratio of anhydrosugar relative to the total of the terminal sugars is 6.2% to 97.5%.

25. The dietary fiber according to claim 1, wherein the value of the following (D) is 0.062 to 0.975:

$$(D) = Y/(X+Y+Z)$$

wherein Z represents the number of sugar chains in which the terminal sugar is a sugar alcohol.

26. The dietary fiber according to claim 1, wherein the value of the following (C) is 0.6 to 0.999:

$$(C) = Z/(X+Z)$$

wherein Z represents the number of sugar chains in which the terminal sugar is a sugar alcohol.

27. The dietary fiber according to claim 1, wherein the ratio of anhydrosugar relative to the total of the terminal sugars is 6.2% to 97.5%, and wherein the value of the following (C) is 0.6 to 0.999:

$$(C) = Z/(X+Z)$$

wherein Z represents the number of sugar chains in which the terminal sugar is a sugar alcohol.

* * * * *